United States Patent

Mattioda et al.

[11] 4,051,244
[45] Sept. 27, 1977

[54] 2,4-DIAMINO 5-BROMO 6-CHLORO PYRIMIDINES, PROCESS FOR THEIR PREPARATION AND USE AS PHARMACEUTICALS

[75] Inventors: Georges Dominique Mattioda, Deuil-la-Barre; Francois Louis Albert Rocquet, Viarmes, both of France

[73] Assignee: Mar-Pha Societe d'Etudes et d'Exploitation de Marques, Paris, France

[21] Appl. No.: 687,972

[22] Filed: May 20, 1976

[30] Foreign Application Priority Data

May 23, 1975 France .................................. 75.16088

[51] Int. Cl.² ................ A61K 31/495; A61K 31/505; C07D 239/00
[52] U.S. Cl. .......................... 424/250; 260/256.4 N; 424/251
[58] Field of Search .................... 424/250, 251; 260/256.4 N

[56] References Cited

U.S. PATENT DOCUMENTS

| | | | |
|---|---|---|---|
| 3,259,623 | 7/1966 | Kober et al. | 260/256.4 N |
| 3,892,554 | 7/1975 | Schneider | 260/256.4 N |
| 3,932,408 | 1/1976 | Eck et al. | 260/256.4 N |

*Primary Examiner*—Stanley J. Friedman
*Attorney, Agent, or Firm*—Beveridge, DeGrandi, Kline & Lunsford

[57] ABSTRACT

Compounds of the general formula

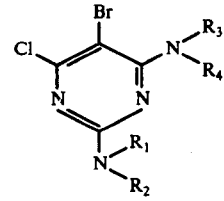

(I)

wherein $R_1$ and $R_3$ represent hydrogen or alkyl containing 1 to 4 carbons; $R_2$ and $R_4$ represent hydrogen, alkyl containing 1 to 8 carbons, dialkylaminoalkyl or aryl,

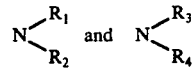

may also represent the piperazinyl group which may be substituted in the 4 position by methyl, phenyl or benzyl.

Compounds have pharmaceutical utility.

17 Claims, No Drawings

2,4-DIAMINO 5-BROMO 6-CHLORO PYRIMIDINES, PROCESS FOR THEIR PREPARATION AND USE AS PHARMACEUTICALS

The present invention relates to new 2,4-diamino 5-bromo 6-chloro pyrimidines of the formula:

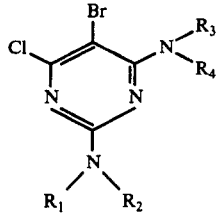
(I)

in which $R_1$ and $R_3$ represent hydrogen or alkyl containing from 1 to 4 carbons; $R_2$ and $R_4$ represent hydrogen, alkyl containing 1 to 8 carbons, dialkylaminoalkyl or aryl;

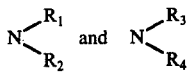

may also represent piperazinyl groups which may be substituted in position 4 by methyl, phenyl or benzyl.

These compounds may be used in pharmaceutical compositions.

The products of formula (I) may in principle be prepared by condensing the amines of formula

with 2 amino 4,6-dichloro 5-bromo pyrimidine and its N-substituted derivatives. It has been determined however, that this method is not considered practicable since it often leads to mixtures of products in which bromine is eliminated.

Now, it has been found, according to the present invention, that the products of formula (I) can be readily obtained by using as starting material 2,4-diamino 5-methylthio 6-chloro pyrimidines of the formula:

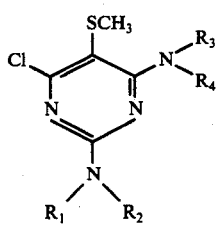
(II)

in which $R_1$, $R_2$, $R_3$ and $R_4$ have the same meaning as in formula (I).

The preparation of the compounds of formula (II) has been described in French application Nos. 73 24 874 and 73 24 875 of July 6, 1973.

The process according to the present invention consists in treating 5-methylthio pyrimidines of formula (II) in a mixture of water and a water miscible solvent, in a homogenous phase, by a solution of bromine in water or in a water miscible solvent. The reaction is effected preferably at moderate temperature, between 0° and 50° C, in a neutral or acid medium, employing a quantity of bromine corresponding to the stoechiometric quantity which is necessary to the reaction represented as follows:

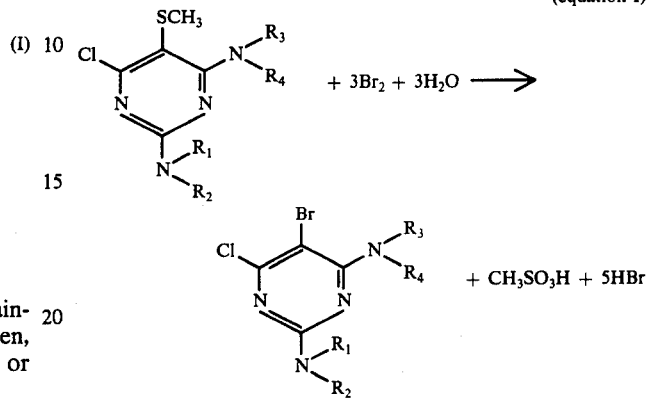
(equation I)

As water miscible solvent, tetrahydrofuran, dioxane or acetic acid may be used. It is within the scope of the invention to utilize instead of the bromine solution, a solution of an oxygen derivative of bromine such as, for example, an aqueous solution of the hypobromite of an alkali metal e.g. Na or K.

After the reaction, the medium is neutralized by the addition of a solution of sodium hydroxide. The product is obtained is extracted with a water insoluble organic solvent such as chloroform, dichlorethane, ethylacetate or ether. The product may be re-crystallized after evaporation of the solvent and transformed into water soluble salt. Yields of isolated pure products are not less than 60%.

The following examples illustrate the invention without limiting it.

EXAMPLE 1

2-methylamino-4-(N-methylpiperazinyl) 5-bromo 6-chloro pyrimidine (1.)

31 g of 2-methylamino 4-(N-methylpiperazinyl) 5-methylthio 6-chloro pyrimidine are dissolved in a one liter vessel in 108 ml of water and 108 ml of acetic acid. Subsequently, 145.5 ml of a solution of bromine in acetic acid is added in 1 hour, 30 minutes, at ambient temperature. This solution contains 40 g of bromine for every 100 ml of acetic acid. A precipitate is formed. At the end of the addition of the bromine, there is added 480 ml of 30% sodium hydroxide solution and the mixture is extracted twice by 450 ml of chloroform. The chloroformic solution is washed twice by 300 ml of water, dried on sodium sulfate and then evaporated. The residue is re-crystallized in 450 ml of ethylacetate. There is obtained 21 g of the above-mentioned product (1) in the form of white crystals. Melting point = 158° C. Yield 63%.

| Analysis for $C_{10}H_{15}N_5ClBr$ | | |
| --- | --- | --- |
| | % | |
| C | H | N |
| calculated 37.50 | 4.72 | 21.87 |
| obtained 37.70 | 4.80 | 21.90 |

On the contrary if, 4,6-dichloro, 2-methylamino 5-bromo pyrimidine is condensed with N-methylpiperazine in toluene, at reflux temperature and in the presence of triethylamine, the desired product cannot be isolated.

EXAMPLE 2

2-(N-methylpiperazinyl) 4,isopropylamino 5-bromo 6-chloro pyrimidine (2)

31.5 g of 2(N-methylpiperzinyl) 4-isopropylamino 5-methylthio 6-chloro pyrimidine are dissolved in 100 ml of acetic acid. The temperature of the medium being 10° C. 278 ml of an aqueous solution of sodium hypobromite (1.08 mole/liter) is run in within one hour. The solution is subsequently made alkaline by way of a 30% sodium hydroxide solution and is extracted three times with chloroform. The chloroformic solution is washed in water, dried and is evaporated. The residue thus obtained constituted by the above-mentioned product (2), weighs 32 g. This residue is dissolved in ethanol and transformed, by the addition of hydrochloric acid, to the monohydrochloride which is re-crystallized in methylethylacetone. Thus, with a yield of 64%, there is obtained the monohydrochloride of monohydrated 2-(N-methylpiperazinyl) 4(isopropylamino) 5-bromo 6-chloro pyrimidine which has a melting point of 230° C.

| Analysis for $C_{12}H_{19}N_5ClBr . HCl . H_2O$ | | |
|---|---|---|
| | % | |
| C | H | N |
| calculated 35.74 | 5.50 | 17.38 |
| obtained 35.91 | 5.27 | 17.38 |

The 2-N-methylpiperazinyl) 4-isopropylamino 5-methylthio 6-chloro pyrimidine, starting product may be prepared according to the process described in example 2 of French application No. 73 24 874, by the reaction of isopropylamine with 2,4,6-trichloro 5-methylthio pyrimidine and the reaction of the mixture of dichloro isomers formed with N-methyl piperazine. Thus there is obtained a mixture of 2(N-methylpiperazinyl) 4-isopropylamine 5-methylthio 6-chloro pyrimidine and 4-(N-methylpiperazinyl) 2-isopropylamino 5-methylthio 6-chloro pyrimidine. This mixture is dissolved in methylethylketone. By cooling of the solution thus obtained at 0° C, the 4-(N-methylpiperazinyl) 2-isopropylamino 5-methylthio 6-chloro pyrimidine is precipitated, separated by filtration, and then by cooling at −50° C, the 2-(N-methylpiperazinyl) 4-isopropylamino 5-methylthio 6-chloro pyrimidine is precipitated. This compound is separated by filtration and re-crystallized in ethanol at 60%. It is then under the form of a solid melting at 65° C.

EXAMPLES 3 to 9

According to the methods in examples 1 and 2, but starting with the corresponding compounds of formula (II), the undermentioned compounds of formula (I) are prepared

| | | Compound of formula (I) | | | |
|---|---|---|---|---|---|
| Ex. No. | $R_1$ | $R_2$ | $-N\begin{matrix}R_3\\R_4\end{matrix}$ | Melting Point ° C | Yield % |
| 3 | H | isopropyl | N-methylpiperazinyl | 185 (base) | 77 |
| 4 | H | n $C_7H_{15}$ | identical | 179 (hydrochloride) | 64 |
| 5 | H | $C_2H_5$ | N-benzylpiperazinyl | 110 (base) | 65 |
| 6 | H | H | N-methylpiperazinyl | 217 (base) | 68 |
| 7 | $CH_3$ | p-tolyl | identical | 92 (base) | 75 |
| 8 | $C_2H_5$ | $C_2H_5$ | identical | 74 (base) | 63 |
| 9 | $CH_3$ | p-tolyl | (diisopropylamino-ethyl)amino | 185 (hydrochloride) | 65 |

TOXICOLOGICAL PROPERTIES

The toxicities of the products according to the invention have been determined on the mouse CD 1 (Charles River) by intravenous and oral methods. The lethal doses 50% (LD 50) are calculated by the cumulative method of Reed J. J. and Muench, H. (Am. J. Hyg. 27, 493, 1938).

The following table shows the results obtained:

| | LD 50 (mg/kg) in the mouse | |
|---|---|---|
| Example | intravenous | oral |
| 1 | 55 | 100 |
| 2 | 83 | 675 |
| 9 | — | 675 |
| 4 | — | sup. 900 |
| 7 | 83 | atox 900 |
| 6 | 48 | 600 |
| 3 | 86 | 200 |

The products of the invention show little toxicity towards the mouse.

PHARMACOLOGICAL PROPERTIES

1. Anti-ulcer Activity

The anti-ulcer properties of the products according to the invention are shown in the rat CD (Charles River) by acute oral administration using two techniques.

The first technique studies the activity of the product in connection with the experimental ulcer induced by reference according to Brodie, D. A. (Gastroenterology, 43, 675, 1962). The result is expressed by a DA 50 which represents the dose in mg/kg capable of protecting 50% of the animals against the least trace of ulceration of the mucous gastric system.

The second studies the activity of the product in connection with the constraint ulcer according to Rossi, G., Bonfils, S., Leifooche, G. and Lambling A. (C.R. Soc. Biol. 150, 2124, 1956). The result is expressed by a DE 50 which represents the dose of the substance in mg/kg capable of decreasing by 50% the ulcerating effect caused by the 24 hours constraint.

The results obtained with the products of the invention are shown hereunder:

| Example | Protection against the ulcer induced by reserpine in a rat DA 50 (mg/kg) p.o. | Protection against constraint ulcer DE 50 (mg/kg) p.o. |
|---|---|---|
| 2 | 100 | — |
| 9 | 300 | — |
| 4 | sup. 100 | — |
| 7 | sup. 100 | — |
| 6 | sup. 100 | — |
| 3 | 20 | 12 |

The products of examples 2 and 3 show outstanding antiulcer properties. The range of about 10 to 300 mg/kg is especially useful.

2. Anti-spasmodic Activities

The anti-spasmodic properties of the compounds according to the invention are shown by use of the technique of Magnus, R. (Ges. Physiol. 102, 123, 1904) in connection with the spasms of the isolated duodenum of a rat caused by either acetylcholine to research an effect of neurotropic type or by barium chloride to research an effect of musculotropic type.

The results, shown hereunder, are expressed by a CE 50 which represents the concentration of product in mg/l capable of decreasing by 50% the amplitude of spasms thus induced.

| Example | Spasms induced by acetyl-choline CE 50 (mg/l) | Spasms induced by barium chloride CE 50 (mg/l) |
|---|---|---|
| 1 | 6 | 2.3 |
| 2 | 5.5 | 3 |
| 4 | 1.4 | 1.3 |
| 7 | 1.4 | 0.6 |
| 6 | 4 | 0.2 |
| 3 | 1.8 | 0.6 |

The compounds present spasmolytic effects, both musculotropic and neurotropic, which are very interesting, particularly those of examples 6, 7, 3 and 4. The range of concentration of from 0.1 to about 7 is especially useful.

3. Anti-emetic Properties

The anti-emetic properties of the compounds according to the invention are shown by oral way in the mongrel dog in tests in which vomitings are induced by apomorphine according to Chen, G. and Ensor, C. (J. Pharmacol exp. Ther. 98, 24, 1950).

The results are expressed by a DE 50 which represents the dose of product capable of diminishing by 50% the number of vomitings induced by the agent.

The product of example 1 shows a DE 50 of 1 mg/kg, the product of example 2 a DE 50 above 5 mg/kg and the product of examples 3 a DE 50 of 1.4 mg/kg. The products of examples 1 and 3 thus show a very important anti-emetic activity. The range of dose of 0.5 mg to 5 mg/kg is useful for this purpose.

4. Anti-serotonine Activity

The anti-serotonine properties of the compounds according to the invention are shown in vitro and in vivo.

In vitro, the action of the products on the spasms induced by the serotonine in the isolated uterus of a rat (rat CD Charles River) is shown, according to the technique of Fanchamps, A., Doepfner, W., Weidman, H. and Cerletti, (A. Schw. Med. Worsch. 90, 1040, 1960).

The results, shown in the table hereunder, are expressed by a CE 50 which represents the concentration in mg/1 of the product capable of decreasing by 50% the amplitude of spasms induced by the serotonine.

In vivo, the products are applied by intra-venous way to anesthesized Albinos Hartley guinea-pigs. A method originated from Konzett, H. and Rossler, R. is employed (Naunyn. Schmiedeberg's Arch. exp. Path. Pharmakol, 195, 71, 1940). The results, shown in the table hereunder, are expressed by a DE 50 which represents the dose capable of reducing by 50% the amplitude of bronchospasms induced by the administration of serotonine.

| Example | Spasms of isolated uterus of rat induced by serotonine CE 50 (mg/l) | Bronchospasms using serotonine in guinea pigs DE 50 (mg/kg) i.v. |
|---|---|---|
| 1 | 0.004 | 0.08 |
| 2 | 0.07 | 0.45 |
| 9 | 0.33 | — |
| 4 | 0.35 | — |
| 7 | 0.05 | — |
| 6 | 0.05 | — |
| 3 | 0.004 | 0.85 |

The compounds of the invention present a very high anti-serotonine activity, in particular those of examples 1 and 3.

The anti-serotonines are very helpful in the treatment of migraines of various type. Therefore the antagonistic properties towards the serotonine of the products according to the invention can be very helpful pariticularly in the case of digestive migraines, beside other activities on the digestive tract.

5. Inhibiting Effects of the Phosphodiesterases of the Brain

Many works attribute a very important function to the cyclic AMP in the neuronal functions. The cyclic AMP is actually present in the central nervous system in a proportion which is higher to that in other tissues and furthermore, the brain possesses relatively high adenylcyclasic activities and phosphodiesterasic activities (Breckenridge, B. M. and Johnston, R. E. Jour. histochem. and cytochem 1969, 17, 505; Weiss, B. Costa, E. Biochem. Pharmacol., 1968, 17, 2107; Williams, R. H., Little, S. A., Ensinck, J. W. Am. J. Med. Sci. 1969, 258, 190). As far as the cerebral phosphodiesterases are concerned, it has been shown that a certain number of psychotropes used in therapy function as inhibitors of these enzymes (Beer, B. and Chasin, M. Clody, D. E., Vogel, J. R., Horovitz, A. T., Sciences, 1972, 175, 428).

The phosphodiesterasic activity is shown by the method of Kukovetz E. R. and Poech, G. (Arch. Pharmakol. 1970, 267, 189) by utilizing the supernatant part obtained after centrifugation at 10,000 G of the brain of male rats CD (Charles River).

The inhibiting action of the compounds according to the invention on the cerebral phosphodiesterases has been tested and expressed by an inhibiting concentration 50% (CI 50) in micromoles. The product of example 2 presents an interesting inhibiting action since its CI 50 is set at 40 micromoles.

THERAPEUTIC TREATMENT USES

The compounds according to the invention and their pharmaceutically acceptable salts may be used in the therapy of human beings requiring therapeutic treatment by internally administering to said human being a amount effective to produce the desired result. The compounds may be used in the form of pills, capsules, gelatin-coated pills, suppositories, solutions for oral ingestion or injectable solutions etc. as psychotropic anti-ulcer, antispasmodic, anti-emetic or anti-serotonine agents.

The posology depends on the effects sought and on the way of administration. For example, orally it may be between 50 and 3000 mg per day of active substance with unitary doses going from 10 to 500 mg.

The present invention includes within it the method of treating ulcers for anti-ulcer therapy in a human requiring such therapy, which is carried out by internally administering to the human an amount effective to produce the anti-ulcer effect of a compound of the formula (I). Similarly, the invention includes the method of producing anti-spasmodic therapy in a human requiring such therapy by internal administration to the human in an amount effective to product the desired anti-spasmodic effect of the compounds of the formula (I).

Still further, the invention includes the method of producing anti-emetic therapy and anti-serotonine activity. Also the present invention includes the method of psychotropic therapy in a human requiring such therapy.

The pharmaceutical compositions of this invention will contain the active compound together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerole solutions can also be employed as liquid carriers, particularly for injectable solutions. Suitable pharmaceutical excipients include starch, glucose, lactose, sucrose, gelatine, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the human. While oral adminstration is a very effective form of administration, other modes can be employed.

We claim:

1. A compound of the general formula:

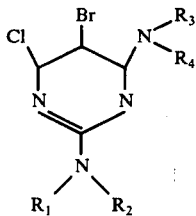

in which $R_1$ represents hydrogen or alkyl containing from 1 to 4 carbons, $R_2$ represents hydrogen, alkyl having 1 to 8 carbons, dialkylaminoalkyl or aryl, and

is piperazinyl which may be substituted in position 4 by methyl or benzyl, or when $R_3$ represents hydrogen or alkyl having 1 to 4 carbons, and when $R_4$ represents hydrogen, alkyl having 1 to 8 carbons, dialkylaminoalkyl or aryl, then

is piperazinyl which may be substituted in position 4 by methyl or benzyl.

2. A compound as defined in claim 1 which is 2-methylamino 4-(N-methylpiperazinyl) 5-bromo 6-chloro pyrimidine.

3. A compound as defined in claim 1 which is 2-(N-methylpiperazinyl) 4-isopropylamino 5-bromo 6-chloro pyrimidine.

4. A compound as defined in claim 1 which is 2-isopropylamino 4-(N-methylpiperazinyl) 5-bromo 6-chloro pyrimidine.

5. A compound as defined in claim 1 which is 2-n heptylamino 4-(N-methylpiperazinyl) 5-bromo 6-chloro pyrimidine.

6. A compound as defined in claim 1 which is 2-ethylamino 4-(N-benzylpiperazinyl) 5-bromo 6-chloro pyrimidine.

7. A compound as defined in claim 1 which is 2-amino 4-(N-methylpiperazinyl) 5-bromo 6-chloro pyrimidine.

8. A compound as defined in claim 1 which is 2-(N-methyl N-p-tolyl) amino 4-(N-methylpiperazinyl) 5-bromo 6-chloro pyrimidine.

9. A compound as defined in claim 1 which is 2-diethylamino 4-(N-methylpiperazinyl) 5-bromo 6-chloro pyrimidine.

10. The compound 2-isopropylamine 4-(N-methylpiperazinyl) 5-bromo 6-chloro pyrimidine.

11. A composition for use as an anti-ulcer, anti-spasmotic, anti-emetic, anti-serotonine or psychotropic agent, comprising a compound as defined in claim 1 with a pharmaceutically acceptable carrier.

12. A pharmaceutical preparation in unit dosage form adapted for administration to obtain anti-ulcer activity comprising per unit dosage an amount effective to produce said therapy within the range of about 10 to 500 mg of a compound of claim 1 in a pharmaceutically acceptable carrier therefor.

13. A composition for use as an anti-ulcer comprising a compound as defined in claim 1 with a pharmaceutically acceptable carrier.

14. A composition for use an anti-ulcer comprising a compound as defined in claim 1 in a unit dosage form within the range of about 10 to about 500 mg in a pharmaceutically acceptable carrier.

15. A method for producing anti-ulcer therapy in a human requiring such therapy which comprises internally administering to said human an amount effective to produce anti-ulcer therapy of a compound of the formula of claim 1.

16. A method of producing anti-spasmotic therapy in a human requiring such therapy which comprises internally administering to said human an amount effective to produce anti-spasmotic acitivity in the human of a compound of the formula of claim 15.

17. A method for producing anti-ulcer therapy in a human requiring such therapy which comprises internally administering to said human an amount in unit dosage form effective to produce anti-ulcer activity within the range of about 10 to about 500 mg of a compound as defined in claim 1 in a pharmaceutical acceptable carrier.

* * * * *